United States Patent
Soane et al.

(10) Patent No.: US 9,315,718 B2
(45) Date of Patent: *Apr. 19, 2016

(54) LOW INTERFACIAL TENSION SURFACTANTS FOR PETROLEUM APPLICATIONS

(71) Applicant: Soane Energy, LLC, Cambridge, MA (US)

(72) Inventors: David S. Soane, Chestnut Hill, MA (US); Rosa Casado Portilla, Peabody, MA (US); John H. Dise, Kirkland, WA (US); Robert P. Mahoney, Newbury, MA (US)

(73) Assignee: Soane Energy, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/608,606

(22) Filed: Jan. 29, 2015

(65) Prior Publication Data

US 2015/0232738 A1    Aug. 20, 2015

Related U.S. Application Data

(60) Division of application No. 13/669,206, filed on Nov. 5, 2012, now Pat. No. 8,969,612, which is a continuation-in-part of application No. 12/958,890, filed on Dec. 2, 2010, now Pat. No. 8,742,165.

(60) Provisional application No. 61/285,385, filed on Dec. 10, 2009.

(51) Int. Cl.
*C09K 8/584* (2006.01)
*C10G 1/04* (2006.01)
*C10G 21/16* (2006.01)

(52) U.S. Cl.
CPC . *C09K 8/584* (2013.01); *C10G 1/04* (2013.01); *C10G 21/16* (2013.01)

(58) Field of Classification Search
None
See application file for complete search history.

(56) References Cited

U.S. PATENT DOCUMENTS

| | | | |
|---|---|---|---|
| 3,522,179 | A | 7/1970 | Le Suer |
| 5,637,557 | A | 6/1997 | Jahnke et al. |
| 5,798,331 | A | 8/1998 | Anderson et al. |
| 7,572,757 | B1 | 8/2009 | Gupta et al. |
| 8,920,656 | B2 | 12/2014 | Stokes et al. |
| 2004/0042983 | A1 | 3/2004 | Harichian et al. |

FOREIGN PATENT DOCUMENTS

DE        3913857 A1    10/1990

OTHER PUBLICATIONS

Nierengarten, J.-F., et al., "Macrocyclization on the Fullerene Core: Direct Regio- and Diastereoselective Multi-Functionalization of [60]Fullerene, and Synthesis of Fullerene-dendrimer Derivatives," Helvetica Chimica Acta, 80(7): 2238-2276 (1997).

(Continued)

*Primary Examiner* — Karl J Puttlitz
(74) *Attorney, Agent, or Firm* — Elmore Patent Law Group, PC; Mahreen Chaudhry Hoda; Carolyn S. Elmore, Esq.

(57) ABSTRACT

The invention relates to a class of novel surfactants that have utility in the recovery and/or extraction of oil.

4 Claims, 2 Drawing Sheets

(56) References Cited

OTHER PUBLICATIONS

Nierengarten, J.-F., et al., "Regio- and Diastereoselective Bisfunctionalization of C60 and Enantioselective Synthesis of a C60 Derivative with a Chiral Addition Pattern," Angew. Chem. Int. Ed. Engl., 35(18): 2101-2103 (1996).

Database CAPLUS Chemical Abstracts Service, Columbus, Ohio, US; Database Accession No. 1991:482097, Abstract of DE 3913857, Agfa-Gevaert A.-G., Germany, Nittel et al., Oct. 31, 1999.

Machine Translation of DE 3913857.

LOW INTERFACIAL TENSION SURFACTANTS FOR PETROLEUM APPLICATIONS

RELATED APPLICATIONS

This application is a divisional of U.S. application Ser. No. 13/669,206, filed Nov. 5, 2012, which is a continuation-in-part of U.S. application Ser. No. 12/958,890, filed Dec. 2, 2010, which application claims the benefit of U.S. Provisional Application No. 61/285,385, filed Dec. 10, 2009. The entire teachings of the above applications are incorporated herein by reference.

FIELD OF THE APPLICATION

The application relates generally to surfactants useful for petroleum applications.

BACKGROUND

A number of problems in the petroleum industry derive from the viscosity, surface tension, hydrophobicity and density of crude oil. Heavy crude oil in particular, having an API gravity of less than 20 degrees, is difficult to transport due to its viscosity, and is difficult to remove from surfaces to which it has adsorbed, due to its hydrophobicity and immiscibility with water. Extra-heavy crude oil or bitumen, having an API gravity of less than 10 degrees, is heavier than water, so that it can sink to the bottom of a water formation, causing subsurface contamination.

The properties of crude oil contribute to the limitations of oil recovery from traditional oil fields. Conservative estimates suggest that 30% of the technically recoverable oil in U.S. oil fields is inaccessible due to the adsorption of the residual oil to porous geologies. Technologies to unlock the oil in these so-called "dead" wells presently involve the use of hot water injections with expensive surfactants, chemistries that are applied to overcome the hydrophobicity of the adsorbed oil so that it can be mobilized.

The properties of crude oil also contribute to the difficulty of environmental remediation following, for example, an oil spill onto a body of water. The high interfacial tension causes the oil to float on the water and adhere to plants, animals and soil. As the aromatic constituents of the oil evaporate, the heavier residues can sink, contaminating the subsurface structures. Current treatment of spilled oil on water surfaces relies on time-consuming and expensive biological degradation of the oil. Thick, adherent crude oil cause environmental problems in the oil fields as well. Oil deposits attached to vehicles and equipment must be cleansed with jets of hot water and caustics.

The viscosity of heavy crude oil makes the substance difficult and expensive to transport to upgrading facilities. Because of its viscosity, a significant amount of energy is required to pump it through pipelines to a refinery. Furthermore, the viscosity affects the speed at which the heavy crude oil can be pumped, decreasing the overall productivity of an oil field. Exploiting certain oil fields or other oil deposits may be economically unfeasible to develop at present because of the transportation-related costs.

Crude oil, as it is produced, is typically associated with connate water that can form a stable emulsion with the oil in multiple phases, including solid-in-oil dispersions, water-in-oil emulsions, and oil-in-water-in-oil emulsions. Certain hydrocarbon molecules found in heavy crude oils can act as emulsifiers to stabilize the various species of water plus oil emulsions. As an example, asphaltenes and high naphthenic acids, along with submicron sized solid particles such as silica, clay or other minerals, can stabilize emulsions such as water-in-oil emulsions where the heavy crude oil fluid comprises the continuous phase. Asphaltenes are high-molecular weight, complex aromatic ring structures that can also contain oxygen, nitrogen, sulfur or heavy metals. As polar molecules, they tend to bond to charged surfaces, especially clays, leading to formation plugging and oil wetting of formations. Asphaltenes tend to be colloidally dispersed in crude oils, stabilized by oil resins.

Asphaltenes, paraffinic waxes, resins and other high-molecular-weight components of heavy crude exist in a polydisperse balance within the heavy crude fluid. A change in the temperature, pressure or composition can destabilize the polydisperse crude oil. Then the heavy and/or polar fractions can separate from the oil mixture into steric colloids, micelles, a separate liquid phase, and/or into a solid precipitate. The asphaltene micelles can be destabilized during well treatments, e.g., acidizing or condensate treatments, leading to asphaltene precipitation. Asphaltene precipitation causes problems all along the crude oil process. Asphaltene precipitation becomes increasingly problematic when crude oil is processed, transported, or stored at cooler temperatures, because the heavier components of crude oil (e.g., asphaltenes and naphthenic acids) that remain dissolved in the heavy crude under high temperatures and pressures are no longer supported in that state as the conditions change. When the heavy crude oil cools to ambient atmospheric temperatures, these components can precipitate out of the crude oil itself and lodge at the bottom of a storage vessel or tank to form a viscous, tarry sludge. These components also become available as emulsifying agents to sustain water-in-oil emulsions. The emulsion layer has a higher density than light crude, so that it tends to sink to the bottom of storage vessels along with the heavy oil components and associated clay/mineral solids, contributing to the buildup of oil sludge, a thick waste material formed from the various deposits sedimenting out from a crude oil mixture.

As mentioned previously, sludge forms when heavier components of crude oil separate from the liquid hydrocarbon fractions by gravity and sink to the bottom of the vessel. Components of the sludge can include usable hydrocarbons along with the aforesaid entrained water as a water-in-oil emulsion, along with a multitude or organic and inorganic components and contaminants. As the heavier elements in the stored oil continue to migrate to the vessel bottom, the sludge becomes increasingly viscous over time. Any given storage vessel can thus contain a significant amount of sludge, which can diminish storage space for useful crude oil and which can otherwise reduce the efficiency of storage tank operation. Sludge may also require removal if the storage vessel is to be maintained, repaired or inspected.

Many approaches have been proposed for preventing the formation of sludge in oil storage vessels such as oil tanks and oil tankers, and for removing sludges and oily sediments that have formed. In particular, it is desirable to recapture valuable hydrocarbons from the sludge as part of the removal process. The two dominant systems for sludge removal are surfactant-based approaches and solvent-based approaches. In surfactant-based systems, aqueous solutions are used to treat the sludge and coalesce the water droplets emulsified within the oil matrix. The particular surfactant is designed to overwhelm the surface energy that is created by the asphaltene/naphthenic acid molecules and return the aqueous portion to a more-native interfacial tension with organics. Current surfactant additives have been shown effective but have commercial limitations because of either high dosage requirements or ineffective solids interactions. Solvent systems typically use a mixture of known aromatic and aliphatic-based organics to decrease the viscosity of the heavier oil fractions and cause phase separation. Issues of cost and toxicity, however, have been raised with the use of solvent-based approaches.

The development of a technology that can provide emulsion and favorable transport properties while maintaining the ability to demulsify on demand, all under variable conditions of salinity, temperature, pH, etc., remains unmet in the art. Such a technology would have wide reaching impact across the oilfield chemical sector in applications such as those mentioned above, particularly if the material could be inexpensively produced and could be applied to a variety of oil types.

Additional uses for a surfactant technology in the oil industry arise from the problems posed by oil well drilling. When drilling oil or gas wells, a drilling fluid, referred to as a "drilling mud," is circulated downwardly through a pipe to reach the drill bit, lubricating it and carrying away the cuttings from the drilling process. The clean drilling mud is injected through a series of pipes called the drill string to reach the bit, and then flows back up to the surface in the annular area between the drill string and the inside of the wellbore carrying the cuttings and other particulate matter. The drilling mud can be water-based or oil-based. Oil-based drilling fluids include as their base material any of a number of natural or synthetic oils, including petroleum fractions, synthetic compounds, blends of natural and synthetic oils, along with a variety of performance-enhancing additives. Following drilling, the wellbore annulus must be cleaned to remove drilling fluids, gelled drilling fluid, residual additives from drilling fluids, and the like. One cleaning process can take place before the casing and cementing operations are done, and another cleaning process is done after the casing is installed. The casing must be cleaned to a water-wet condition with no oil sheen. Oil-based drilling fluids, especially synthetic based muds (SBMs), are particularly difficult to remove from the surfaces they contact. These oil-based fluids can form invert emulsions upon contact with water, where the continuous phase is predominantly organic, and the discontinuous phase is aqueous. This emulsion will tenaciously coat any surface that it contacts, leading to oil wetting of borehole surfaces, casing surfaces, and the surfaces of other equipment that it contacts.

Wellbore cleaning can involve the use of a sequence of fluids, each having a specific purpose. In designing the sequence for the cleaning process, formulations are selected that give maximum performance while using minimum amounts of material. Also, the fluids must be chemically and physically compatible, so that an earlier one does not interfere with the function of subsequent ones. Cleaning operations must be conducted carefully, so that the clay components of the drilling mud residue do not come into contact with water, thereby forming a thick paste that adds to the difficulty of removal. There remains a need in the art, however, for a cleaning system that is effective and efficient in removing drilling mud films and residua from wellbore surfaces. This need is exacerbated by the prevalence of SBMs, which produce harder-to-remove films. There is also a need for a cleaning system that requires less fluid volume than those systems presently in use. In addition, there is a need for a cleaning system that does not require or produce hazardous materials.

SUMMARY

The invention relates to the discovery to surfactant compounds with utility in recovering or extracting oil, such as fossil fuels.

Accordingly, in some embodiments, the invention relates to a compound having the

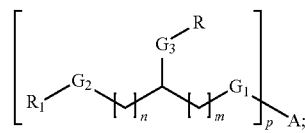

Formula (I)

wherein A is an alkyl, alkenyl, alkadienyl, alkynyl, cycloalkyl, or cycloalkenyl, each optionally substituted;
p is 1 or 2; preferably 2;
m and n are independently 0, 1, 2, 3, 4, or 5;
each of $G_1$ and $G_2$ are independently absent, O, S, $NR_2$, (CO)O, O(CO), CO, $CONR_2$, or $NR_2CO$;
each $R_2$ is independently H or a lower alkyl;
$G_3$ is absent, $(CH_2)_q$ or $G_1$;
q is 1, 2, 3, 4 or 5;
R is a hydrophilic group; and
$R_1$ is a saturated or unsaturated hydrophobic aliphatic group.
In certain aspects, m is 1 or 2 and n is 0 or 1. In some embodiments, at least one of $G_1$ and $G_2$ are present.

In some embodiments, the invention is compound having the Formula (Ia):

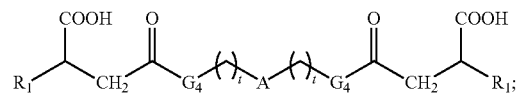

wherein t is 0 or 1;
$G_4$ is O or NH; and A and $R_1$ as defined above.

In an additional embodiment, the invention is directed to a compound of Formula (II):

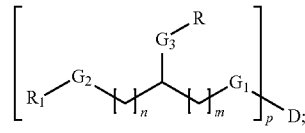

wherein D is an aliphatic polymer;
p is 1 or 2; preferably 2;
m and n are independently 0, 1, 2, 3, 4, or 5;
each of $G_1$ and $G_2$ are independently absent, O, S, $NR_2$, (CO)O, O(CO), CO, $CONR_2$, or $NR_2CO$;
each $R_2$ is independently H or a lower alkyl;
$G_3$ is absent, $(CH_2)_q$ or $G_1$;
q is 1, 2, 3, 4 or 5;
R is a hydrophilic group; and
$R_1$ is a saturated or unsaturated hydrophobic aliphatic group.
In certain embodiments, the invention encompasses a compound having the Formula (IIa);

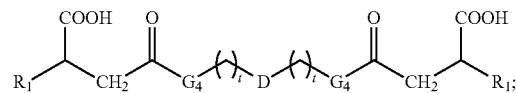

wherein t is 0 or 1;
$G_4$ is O or NH; and D and $R_1$ are as defined above.

In a further aspect of the invention, the compound has the Formula (IIb):

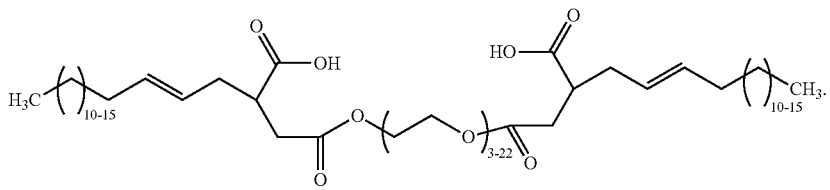

In an additional embodiment, the invention relates to a compound of Formula III:

E—(G$_5$-D$_2$)$_p$;

wherein E is alkyl, alkenyl, alkadienyl, alkynyl, cycloalkyl, cycloalkenyl, aryl and heteroaryl;
G$_5$ is CONH;
D$_2$ is a hydrophilic aliphatic polymer; and
p is 1 or 2.

In yet another aspect, the invention encompasses a compound having the Formula (IV):

D$_2$-N(J)$_2$;

wherein D$_2$ is a hydrophilic aliphatic polymer;
wherein each J is independently selected from the group consisting of hydrogen and the Fragment (A) having the structure shown below;

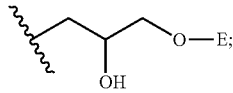

wherein E is a hydrophobic group selected from the group consisting of alkyl, alkenyl, alkadienyl, alkynyl, cycloalkyl, cycloalkenyl, aryl and heteroaryl; and wherein at least one J is the Fragment (A).

The invention also encompasses a compound having the Formula (V):

(J)$_2$N-D$_2$-N(J)$_2$;

wherein D$_2$ is a hydrophilic aliphatic polymer;
each J is independently selected from the group consisting of H and the Fragment (A):

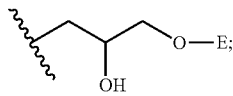

wherein E is a hydrophobic group selected from the group consisting of alkyl, alkenyl, alkadienyl, alkynyl, cycloalkyl, cycloalkenyl, aryl and heteroaryl;
and wherein at least two of J are Fragment (A).

The invention also relates to methods for extracting oil from an oil mixture comprising:
(a) adding a compound of any one of Formula (I), Formula (Ia), Formula (II), Formula (IIa), Formula (IIb), Formula (III), Formula (IV) and Formula (V), or a combination of any of thereof, to an oil mixture, and
(b) collecting the oil.

An oil mixture is a mixture comprising oil and at least one other component. The oil mixture can comprise oil sands, waterborne oil slicks or oil deposits. Further, the methods of the invention can comprise the additional steps of adding water or transporting the mixture via a pipeline. In another embodiment, the compounds and compositions of the invention can be used in methods of degreasing machinery, such as those used in oil or bitumen production.

DETAILED DESCRIPTION

General Formulations

Figure 1:
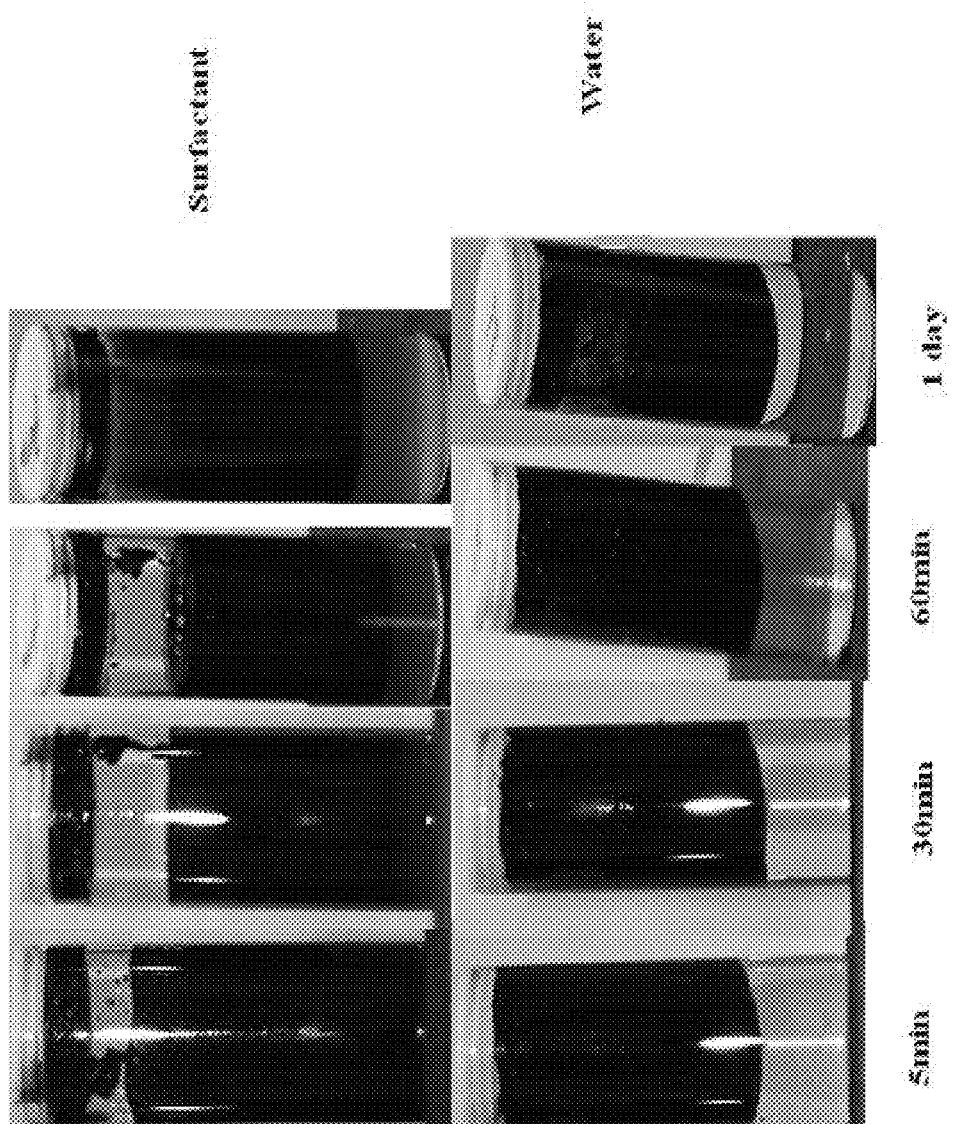
FIG. 1 shows comparison photographs of phase separation.

Disclosed herein are compositions, systems and methods related to ultra-low interfacial tension ("IFT") surfactants for applications in the petroleum industry. In certain embodiments, the present disclosure is based on the discovery that multiple aliphatic-based functionalities can be incorporated onto a single surfactant molecule. This molecule can include functionality that allows it to be either surface-active or surface-inactive by adjusting or "tuning" the surfactant by means of an adjustment of a parameter such as temperature or pH. Preferably, the application of a single-molecule, switchable surfactant system is prepared in aqueous solution. Suitable surfactant solutions for application in enhanced oil recovery will also display very low interfacial tension values with both crude oil as well as organics with aliphatic and aromatic character. Additionally, surfactant solutions exhibiting only pH switchability will remain in solution at elevated temperatures, so that they can be inserted into underground wells, where temperatures may range between 70-100° C.

For such applications as enhanced oil recovery, the ability to deactivate a surfactant (i.e., "turn it off") would enable the user first to create an emulsion of the petroleum to be recovered, then to transport the oil in an emulsified state, then to easily separate the oil from the emulsion when it has reached its desired destination. Controlling the phase state of an oil deposit could potentially be a useful tool in recovering difficult to access, yet desirable, sources of oil.

In one embodiment, compositions of particular use in these systems and methods can include at least one compound of the Formula (I), Formula (Ia), Formula (II), Formula (IIa), Formula (IIb), Formula (III), Formula (IV) or Formula (V) as described above.

In some aspects of the invention, the compound has the Formula (I), (Ia), (II) or (IIa). The invention encompasses compounds having the Formula (I) or Formula (Ia), wherein A is an alkyl (e.g., a $C_3$-$C_8$ alkyl) or cycloalkyl, each optionally substituted. In another embodiment, A is an alkyl-substituted cyclopentyl or cyclohexyl. Examples of alkyl-substituted cyclohexyl is propylcyclohexyl and ethylcyclohexyl. In additional aspects, the compound has the Formula (I), wherein G$_1$ is selected from the group consisting of O, S, $NR_2$, $C(O)O$, $OC(O)$, $C(O)$, $C(O)NR_2$ and $NR_2C(O)$. In yet additional aspects, the compound has the Formula (I), wherein $G_1$ is selected from the group consisting of $C(O)O$, $OC(O)$, $C(O)$, $C(O)NR_2$ and $NR_2C(O)$. In yet further aspects, $G_1$ is selected from $C(O)O$ and $C(O)NR_2$. In additional aspects, the compound has the Formula (I) wherein p is 1. In yet additional aspects, the compound has the Formula (I) wherein p is 2. In a further aspect, the invention is a compound of Formula (I) wherein m is 1 or 2. In yet additional aspects, the invention is a compound of Formula (I), wherein n is 0 or 1. In yet another aspect, the invention is a compound of Formula (I), wherein R is $C(O)OH$. In a further aspect, the invention is a compound of Formula (I), wherein $R_1$ is selected from the group consisting of $C_5$-$C_{20}$ alkyl, $C_5$-$C_{20}$ alkenyl, and $C_5$-$C_{20}$ alkadienyl.

In other embodiments, the compound has the Formula (II) or (IIa), wherein D is selected from the group consisting of polyethylene glycol, poly(ethylene glycol)/poly(propylene glycol) copolymers, polyethylene glycol methyl ether, polyetheramine and ethylene oxide/propylene oxide block copolymer. In additional aspects, the compound has the Formula (II), wherein p is 1. In a further aspect, the compound has the Formula (II), wherein p is 2. In yet an additional aspect, the compound has the Formula (II), wherein m is 1 or 2, or n is independently 0 or 1, or a combination thereof. The invention also includes the compound of Formula (II), wherein each $G_1$ is independently $OC(O)$, $C(O)O$, $C(O)$, $C(O)NR_2$ or $NR_2C(O)$. In an additional aspect, the compound has the Formula (II) wherein $G_2$ is absent. In a further aspect, the compound has the Formula (II) wherein R is $C(O)OH$.

In certain additional aspects, the compound has the Formula (IIa) wherein D is polyethylene glycol. In yet another aspect, the compound has the Formula (IIa) wherein $R_1$ is selected from the group consisting of $C_5$-$C_{22}$ alkyl, $C_5$-$C_{22}$ alkenyl, and $C_5$-$C_{22}$ alkadienyl. In yet an additional embodiment, the compound has the Formula (IIa) wherein D is polyethylene glycol, $R_1$ is selected from the group consisting of $C_5$-$C_{22}$ alkyl, $C_5$-$C_{22}$ alkenyl, and $C_5$-$C_{22}$ alkadienyl, $G_4$ is O and t is 0. In yet additional aspects, the compound has the Formula (IIa) wherein D is polyethylene glycol, $R_1$ is a $C_5$-$C_{22}$ alkenyl, $G_4$ is O and t is 0. In a further aspect of the invention, the compound has the Formula (IIb):

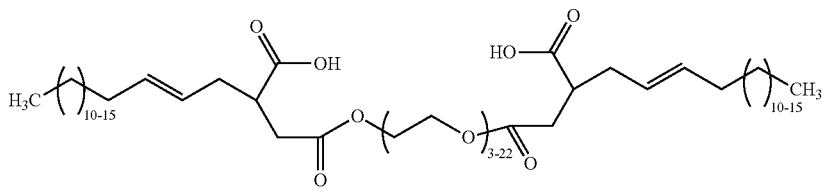

In further aspects, the compound has the structure shown below:

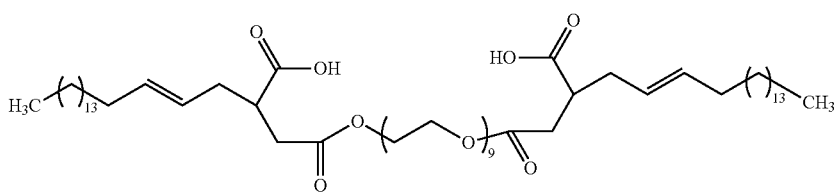

As described above, compounds of Formula (I), (Ia), (II) and (IIa) comprise a hydrophilic portion (substituent R) and a hydrophobic aliphatic group (substituent $R_1$). In some embodiments, the aliphatic groups include saturated or unsaturated carbon chains, preferably between five and twenty units in length, or five and eighteen units in length, or eight and twenty units in length, fifteen and twenty-two units in length, or hydrogen. The carbon chains can optionally be unsaturated and, when present, reside anywhere along the carbon chain. The hydrophilic portion of the inventive compounds can comprise one or more hydrophilic groups or substituents. Hydrophilic portions or groups can be an ionizable groups, including, for example, amines and carboxylic acids. In certain aspects of the invention, the hydrophilic group is $C(O)OH$. Hydrophilic groups also include hydrophilic polymers, including, but not limited to, polyalkylamine, poly(ethylene glycol) or poly(ethylene glycol)/poly(propylene glycol) copolymers. Nonionic hydrophilic materials such as polyalkylamine, poly(ethylene glycol) or poly(ethylene glycol)/poly(propylene glycol) copolymers can be used to increase hydrophilicity or aid stability in salt solutions.

In some embodiments, the surfactant compound has the Formula (III). In certain aspects, $D_2$ is a polymer or copolymer containing ether groups. The invention also encompasses a method for the preparation of a compound having the Formula (III) comprising reacting an aliphatic or aromatic diacid with a polyetheramine. In an additional embodiment, the compound has the Formula (III), wherein E is $C_1$-$C_6$ alkyl.

In an additional embodiment, the surfactant compound has the Formula (IV) or Formula (V) as described above, wherein $D_2$ is a polyether. In certain aspects, E is a $C_5$-$C_{20}$ alkyl, $C_5$-$C_{20}$ alkadienyl or $C_5$-$C_{20}$ alkenyl.

The invention also is directed to methods for the preparation of a compound having Formula (IV) or Formula (V) comprising reacting an amino-containing polyether with an epoxy-containing compound. An example of an amino-containing polyether is a polyetheramine. Non-limiting examples of epoxy-containing compounds are styrene oxide, 2,3-diphenyloxirane, phenyl glycidyl ether, 1-naphthyl 2-oxiranylmethyl ether, and poly[(o-cresyl glycidyl ether)-co-formaldehyde.

In certain aspects, a lower alkyl is a $C_1$-$C_{10}$ alkyl, $C_1$-$C_6$ alkyl, or $C_1$-$C_4$ alkyl.

The compounds described herein can be used as surfactants. In embodiments, these compounds can demonstrate switchable behavior under conditions where pH and/or temperature is varied.

Switchability

In embodiments, the inventive surfactants, such as a compound of Formula (I), (Ia), (II), (IIa), (IIb), (III), (IV) or (V), can demonstrate switchable behavior based on pH, where the surfactant is capable of sustaining an emulsion at a higher pH, but loses its emulsification properties at a lower pH. In embodiments, pH switchable surfactants can comprise an ionizable group and a hydrophobic portion, or an ionizable portion and a hydrophilic and a hydrophobic portion. The ionizable group on the surfactant reacts to changes in pH that impact its emulsification properties. For example, with a decrease in pH, the ionizable group will be in the protonated form and the surfactant molecule will lose its solubility in water solution, thereby losing its emulsification properties. Conversely, if the pH increases, the ionizable group will be in the ionic form and the surfactant molecule will increase its solubility in water solution, thus being capable of sustaining emulsions of oil in water. This behavior is reversible because no functional groups are cleaved in the process. Non-limiting examples of surfactants demonstrating this behavior include surfactants prepared in accordance with Examples 1, 2 and 3 shown below.

able to emulsify oil in water. However, upon increasing the temperature above the cloud point, the surfactants will lose solubility in water solutions and will lose their emulsification properties. The behavior is reversible because no functional groups are cleaved in the process. Non-limiting examples of surfactants demonstrating this behavior are those prepared in accordance with Examples 9, 10, 11 and 13.

In embodiments, surfactants can demonstrate switchable behavior based on changes in temperature and pH. There are trigger points for emulsification capability that are determined by pH and by temperature. Non-limiting examples of such surfactants are those prepared in accordance with Examples 4, 5, 6 and 7 below.

In certain embodiments, temperature switchable behavior can be elicited in compounds having ether groups. For example, PEG or hydroxyl-terminated ethers such as PPO and PEO (e.g., Pluronics) can be reacted with anhydrides such as alkene succinic anhydride (for example, 8, 9, 12 units), and styrene maleic anhydride copolymers. For example, the surfactant can be the product of a reaction between PEG and an alkenylated succinic anhydride. In an additional example, the reaction can be as shown below

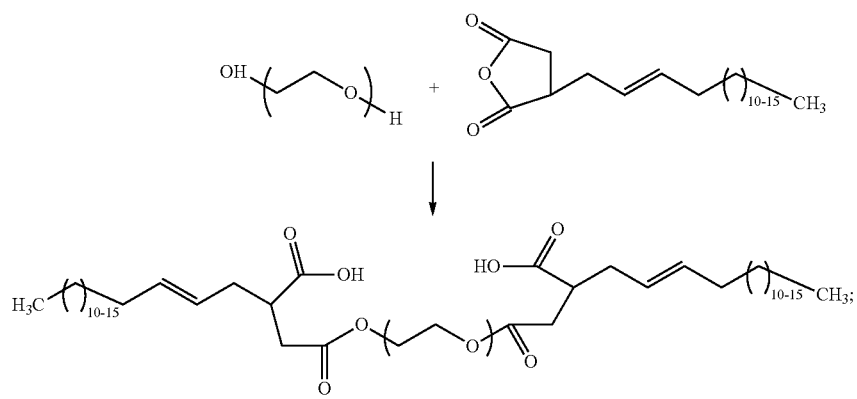

In embodiments, surfactants can demonstrate switchable behavior based on changes in temperature, whereby they are able to stabilize emulsions at temperatures below their cloud points but lose their emulsification properties at temperatures above their cloud points. In embodiments, temperature switchable surfactants will have a hydrophobic portion and a hydrophilic portion mainly containing, for example, ethoxylated groups. Such surfactants can display solubility in water solutions at temperatures below the cloud point and will be wherein it is understood that

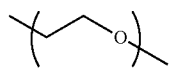

is a polyethylene glycol.

In certain embodiments, the polyethylene glycol has a chain length of 3 to 22. Such a reaction is shown below:

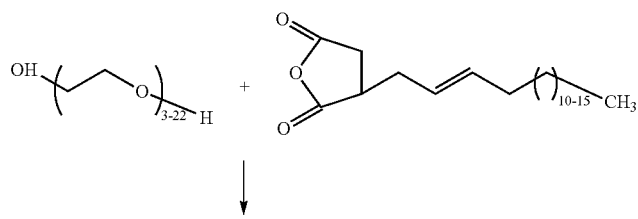

-continued

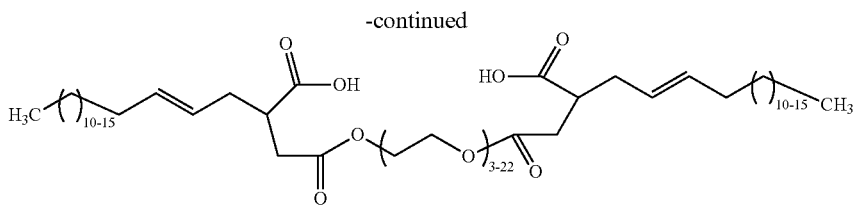

Such a reaction is described in the Exemplification section below, in Examples 4 and 5, for example.

In other aspects of the invention, the hydrophilic portion of the surfactant compounds of the invention include one or more polymers or copolymers containing ether groups. These polymers impart the compounds with a cloud point. The compounds will display solubility in water at temperatures below the cloud point and, as a consequence, are able to emulsify oil. However, upon increasing the temperature over the cloud point, the compounds become less soluble in water and show a decrease in emulsification properties. It is believed that this behavior is reversible because no functional groups are cleaved in the process. Some non-limiting examples of these kinds of compounds can be obtained by reacting:

(i) Amino (primary or secondary)-containing polyethers with epoxy compounds. Examples of amino-containing compounds are: polyetheramines, such as JEFFAMINES® from Huntsman, and other PEG and PPO/PEG containing primary, secondary amines. Examples of epoxy compounds include aryl glycidyl ether, such as: styrene oxide, 2,3-diphenyloxirane, phenyl glycidyl ether, 1-naphthyl 2-oxiranylmethyl ether, and poly[(o-cresyl glycidyl ether)-co-formaldehyde;

(ii) Acid groups with amines or alcohols. Examples include reacting aromatic diacids with a polyether containing (primary or secondary) amine or hydroxy units. Another embodiment is the reaction of a polyethylene glycol-diacid terminated with and aromatic amine or alcohol;

(iii) Copolymerizing monomers that can form polymers with LCST such as N-vinylcaprolactam, isopropyl acrylamide or diethylacrylamide with acrylic acid, followed by reacting the acid with a alcohol or amine groups, preferably the alcohol or amine will be slightly hydrophobic (hexyl alcohol, hexyl amine, octyl alcohol, octyl amine, phenethyl alcohol, etc.).

In some aspects of the invention, the hydrophilic portion of compounds of the invention is a combination of: (i) one or more copolymers containing ether groups, and (ii) one or more ionizable carboxylic acid groups. In this case, the obtained compound has emulsification capabilities that are triggered by a change in pH or temperature. Below a specific pH, the surfactant compound has emulsification properties under certain temperature conditions. However, above that pH, the temperature at which the surfactant has emulsification properties increases. The surfactants are thus tunable based on changes in pH or temperature.

In some embodiments, the hydrophilic portion of the compound comprises an ionizable carboxylic acid group. In yet additional embodiments, the surfactant composition comprises a compound of the invention in a basic, aqueous solution. In certain additional embodiment, the surfactant composition comprises a compound of Formula (II), (IIa) or (IIb) in a basic, aqueous solution. In yet another aspect, the surfactant composition comprising a composition comprises a compound of Formula (II), (IIa) or (IIb) in a solution comprising sodium hydroxide (NaOH). An example a compound with ionized carboxylic acid groups is shown below:

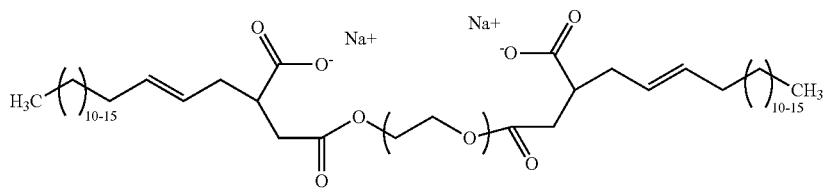

Exemplary surfactants can be synthesized by reacting:
(i) PEG and PPO/PEG (hydroxyl terminated) with aromatic anhydrides. Examples of PEG and PPO/PEG are the PLURONICS®. Examples of aromatic anhydrides are phenyl succinic anhydride;
(ii) Copolymerizing monomers that can form polymers with LCST such as N-vinylcaprolactam, isopropyl acrylamide or diethylacrylamide with acrylic acid followed by reacting a fraction of the acid with a alcohol or amine groups, preferably slightly hydrophobic (hexyl alcohol, hexyl amine, octyl alcohol, octyl amine, Phenethyl alcohol, etc.).

Applications

Environmental Remediation

By taking advantage of the low IFT behavior of the surfactant compounds disclosed herein, such surfactants can be suitable for applications where undesired petroleum products pose an environmental problem. Oil cleanup using surfactants may be required for two different types of contamination. First, as an oil slick dispersant, the surfactant family can be used on waterborne slicks, acting as a dispersing agent. It will act to disperse the oil into the water body itself and encourage biodegradation through natural decomposition means. Additionally, a solution of surfactant can be used to remove physisorbed crude or refined oils from inorganic rocks, sand, or other substrates as an emulsion.

Oil Sands Extraction

Oil sands comprise heavy petroleum products coating sand and clay, an assemblage that is similar to certain artificial composites that are formed during a man-made oil spill, as described above. The surfactant compounds and compositions thereof described herein may be useful for extracting bitumen from the other components of the tar sands material. Currently, mined oil sands are extracted using hot water, a process that causes the less dense bitumen to flow off the sand and float to the surface of a settling tank. This so-called "primary froth" is contaminated with various materials derived from the mined products (solid particles, clay, and sand). Current froth treatment utilizes naphtha, a valuable fraction of purified petroleum, to dilute the bitumen and decrease the viscosity to the point of flowability. This allows solids and water to be removed by settling and centrifugation methods. By using an aqueous solution of surfactant as the dilution medium instead of naphtha, the latter solvent can be replaced with water and surfactant, thus decreasing the cost of purifying the froth. Additionally, when the surfactant-diluted bitumen is recovered from the water, the hydrophilic portions associated with the froth (clay, water, salts) will preferentially partition to the water phase and be separable from the bitumen.

Use of the inventive surfactants in accordance with these systems and methods may further be applied to other aspects of the extraction process, for example in the oil sands strip mining or in-situ operations, where the ability to emulsify the petroleum component of the oil sands ore may enhance the efficiency or economy of separating the bitumen from the insoluble byproducts.

Oil Field Transport Emulsions

Transporting petroleum precursors for further processing is a necessary, though expensive, part of obtaining usable crude oil. When petroleum is obtained as a heavy crude, it needs to be transported to an upgrading facility for conversion to useful petroleum products. Typically, pipeline transport is the most economical means to accomplish this. When oil sands are used as precursors in the production of synthetic crude oil, they are transported for further processing after extraction and froth treatment through pipelines as a naphtha-diluted bitumen so that they can undergo further upgrading processes, including cracking and coking, amongst other standard refining operations. For these types of applications in the petroleum and tar sands industries, the heavy oil or oil precursor materials (respectively) may be transported through pipelines as oil-in-water mixtures or emulsions. It is understood that more viscous matter being sent through pipelines has a greater resistance to flow and consequently requires more energy to move an equivalent distance. Hence, decreasing the viscosity of the flowable matter decreases the amount of pumping energy required, and potentially improves the transit time and the productivity of the overall process. Mixing water with crude oil or bitumen can decrease the viscosity of these latter substances towards the viscosity of water, but only if a water-continuous emulsion is created. The surfactants described herein can compatibilize oil and water into an emulsion that can be pumped with greatly decreased energy requirements and/or increase the throughput of crude oil or oil precursors to their destinations.

Auxiliary Petroleum Applications

There also exist many other opportunities in the oilfield chemical sector for degreasing applications, as can be accomplished with the systems and methods disclosed herein. Periodically, machinery used in oil and bitumen production must be cleaned for maintenance and performance reasons. With petroleum production heading towards heavier crude reserves, the need for an effective degreaser becomes even more acute: exposure to heavier crude oils results in thicker, more adherent oil residues that must be removed during the cleaning/degreasing processes. The surfactants described herein can be an active ingredient in an industrial degreasing formulation for these purposes.

Enhanced Oil Recovery (EOR)

Tertiary oil recovery, also known as "enhanced" or "improved" oil recovery, makes use of low IFT polymers to produce oil from wells that have stopped producing of their own accord. Injection of a low IFT surfactant into one of these less productive wells can stimulate production from the residual oil left adhered to the surface of porous rocks. The compounds described herein are useful as low IFT surfactants for EOR.

Desalting

Desalting refers to the process of removing salts from oil, making the oil more suitable for further refining. Salts, including magnesium chloride, sodium chloride and calcium chloride can be found in crude oil. If allowed to remain in the crude oil during the refinery operation, the salts can dissociate and the chloride ion can ionize to form hydrochloric acid, which, along with various organic acids found in crude oil, contributes to corrosion in refinery equipment. In addition, other metal salts (e.g., potassium, nickel, vanadium, copper, iron and zinc) can be found in the crude oil, also contributing to fouling of the equipment and end-product degradation. Crude oil also contains emulsified water, which contains dissolved salts.

Desalting crude oil takes advantage of the fact that the salts dissolve in a water phase, which is separable from the oil phase. Crude oil naturally contains water in emulsion, as mentioned above. For certain techniques of desalting, additional water may be added to the oil (e.g., in an amount between 5-10% by volume of crude) so that the impurities can further dissolve in the water. The water-in-oil emulsion can be broken with the assistance of emulsion-breaking chemicals and/or by exposing the emulsion to an electrical field that polarizes the water phase, so that the water phase bearing the impurities separates from the petroleum phase. Ethoxylated nonylphenols are a class of nonionic surfactants that have been used for desalting crude oil according to these principles.

The surfactant compounds disclosed herein can facilitate the demulsification of the water-in-oil emulsion, so that the oil phase separates from the water phase, with the water phase carrying the soluble impurities (i.e., the salts). In embodiments, the hydrophilic portion of the surfactant compound can include one or more ionizable carboxylic acid groups that can be ionized at a basic pH (e.g., >8) to produce an emulsion-sustaining material. In another embodiment, the carboxylic acid groups of a compound of Formula (IIa) or (IIb) is ionized at a basic pH (for example, at a pH greater than 8). To destabilize the emulsion, acid may be added, removing the charge stabilization and allowing the two phases to segregate from each other.

Sludge and Tank Bottoms Clean-Up

In accordance with these systems and methods, an aqueous surfactant solution comprising an amphiphilic surfactant can be used to emulsify heavy crude oil components that have settled as a sludge at the bottom of the oil containment vessel. Such a surfactant can be injected into the sludge, thereby forming an oil-in-water emulsion comprising the heavy crude oil components of the sludge, which emulsion can then be removed from the oil containment vessel, thereby desludging it. In embodiments, the sludge to be treated comprises an oil-contaminated sediment that was created by accidental discharge of hydrocarbons onto the ground or a body of water. In embodiments, the sludge to be treated comprises asphaltenes, or it comprises a water-in-oil emulsion.

In embodiments, the aqueous surfactant includes a switchable, "smart" surfactant, which can be injected as an aqueous solution into an oil storage vessel to emulsify the heavy oil sludge into the water phase with minimal agitation. Establishing water as the continuous phase of the emulsion for the sludge can decrease the sludge viscosity so that it can be pumped out of the storage vessel into an alternate containment system. For example, the sludge-in-water emulsion can be directed to a distinct separation vessel, where the emulsion can then be broken, yielding a phase-separate two-component system comprised of crude oil fractions suitable for further refining and recovered water suitable for reuse in similar or other projects.

In embodiments, several steps will be required for the surfactant system. First, the surfactant will be injected into the heavy oil sludge (including the rag layer), so that the surfactant can destabilize the heavy oil-water interface to invert the emulsion into the water phase. In this initial phase, an amphiphilic, water-soluble polymer can be used that is effective at low concentrations. After this is accomplished, the resulting water emulsion can be removed from the subject vessel and relocated, for example to a separation vessel. This may take place as a separate step after the first step has been completed. In other embodiments, however, this can take place during the first step. For example, the water emulsion can be siphoned off as it is formed. As a final step, the water emulsion containing the stabilized oil droplets can be demulsified. A change in the conditions of the water emulsion can change the conformation of the surfactant, so that it breaks into an oil-soluble component and a water-soluble component. The oil-soluble component thus demulsifies the heavy oil droplets, while the water-soluble component remains in the water phase. Surfactant molecules can be designed so that the water-soluble byproduct is non-toxic and environmentally safe. The emulsification and/or separation processes might be carried out at temperatures above ambient, to facilitate flow and emulsification or to cause switching of the surfactant properties.

In embodiments, a surfactant in accordance with these formulations and methods can be formulated as a polymer that can emulsify the heavy crudes, but can decompose into one or more oligomers capable of effecting demulsification. Oligomers suitable for demulsifying can include: polyethylene oxide/polypropylene oxide copolymers, cellulose esters, polyethylene/ethylene oxide copolymers, ethoxylated nonylphenols, and the like. In embodiments, a random linear copolymer can act as the emulsifying agent. Such a copolymer can contain regions of ionic charge, such as a quaternary amine or sulfonate, that would be resistant to the high-salt environment in the sludge. To create the surfactant effect, the copolymer could further contain nonionic regions having hydrophobicity, such as polycarbonate, polystyrene or styrene maleic anhydride. In the copolymer, a demulsifying oligomer (as set forth above) can be covalently attached to the nonionic hydrophobic regions. As a first step using these formulations, the sludge would be emulsified using the surfactants to form an oil-in-water emulsion. The emulsion could then be pumped from the subject tank or other vessel to a suitable separation vessel. Heat could be optionally added. In the separation vessel, the pH could be altered so that the covalent linkage holding the demulsifying moieties in place would be broken. If the covalent bond is a weak one (e.g., an ester bond), it may be altered by adding heat only. For other covalent linkages (e.g., ethers and amides), alkali may need to be added to the emulsion. With the release of the demulsifying agent from its attachment to the polymer, phase separation of oil and water would occur. Water and oil could then be directed for further processing as separate fluid streams.

Wellbore Cleaning

Disclosed herein are compounds and methods that have utility in cleaning wellbores and the like with a multipurpose water-based formulation that can remove films left behind from the use of synthetic base muds, and at the same time leave the wellbore surface in a hydrophilic state. Advantageously, the disclosed formulations can minimize volumes of cleaning materials utilized for wellbore cleanout, reduce the amount of waste material produced and offer tailored formulations for specific films left by different drilling muds. The hydrophilic regions of the surfactant compounds disclose herein can attract aqueous fluids to wash away or break up the oil and the hydrophobic portion can be designed to have high oil affinity.

Contaminated Cuttings

During the drilling process, cuttings are formed that are contaminated with oil. In many situations, they are considered hazardous waste because of their oil content, whether from oil-based drilling fluid or from formation-produced oil. Disposal of these contaminated cuttings is specialized and expensive, because of their hazardous waste status. In embodiments, cuttings generated during the drilling operations can be cleaned using surfactants disclosed herein. Cleaning the cuttings by removing the oil may reduce their hazard burden. The use of switchable surfactants for cleaning cuttings is especially advantageous because the emulsion can be demulsified in a manner that minimizes the contaminated wastewater produced and allows recovery of oil.

The invention is illustrated by the following examples which are not meant to be limiting in any way.

EXAMPLES

Materials

All materials were purchased from Aldrich except those listed below:

PLURONIC® L64, L35 and L31 were obtained from BASF Corporation, Florham Park, N.J. 07932, USA.

JEFFAMINE® ED-900, M-1000, ED-2003, ED-600 were obtained from HUNTSMAN, Austin, Tex. 78752, USA.

Eka SA 210: EKA Chemicals, Inc., Marietta, Ga. 30062, USA.

Example 1

Reaction Between Alkenylsuccinic Anhydride and Aliphatic Alcohol

A reactor was charged with 1,3-butanediol (0.64 g, 7.14 mmol) (Aldrich) and Eka SA 210 brand alkylated succinic anhydride (5 g, 14.28 mmol). The mixture was stirred for about 4 hours at 130° C. under nitrogen. The product was then analyzed by an AVATAR 360 FT-IR ("IR"). The sample was run in the "Attenuated Total Reflectance mode" placing the sample over a Germanium crystal. The IR spectra showed the almost complete disappearance of the initial anhydride peaks due to the carbonyl groups (peaks at 1859 and 1778 cm-1), and the appearance of carbonyl peaks at 1735 and 1704 cm-1 due to the formation of ester and acid respectively.

Other properties of the product were identified as follows:
Solubility in water at 25° C.~1%.
The scheme below illustrates this synthesis:

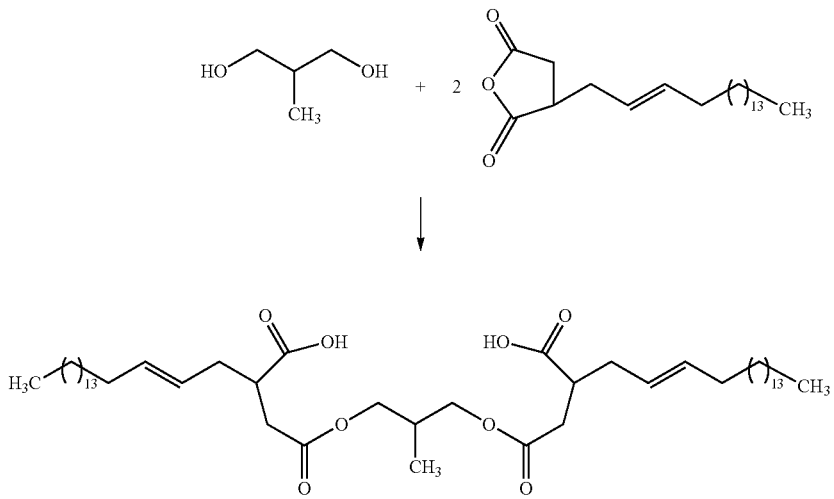

Example 2

Reaction Between Alkenylsuccinic Anhydride and Aliphatic Alcohol

A reactor was charged with neopentyl alcohol (3.482 g, 33.4 mmol) (Aldrich) and 2-(1-nonenyl) succinic anhydride (15 g, 66.87 mmol) (Aldrich). The mixture was stirred for about 1.5 hours at 130° C. under nitrogen. The product was then analyzed by IR. The sample was run in the "Attenuated Total Reflectance mode" placing the sample over a Germanium crystal. The IR spectra showed the almost complete disappearance of the initial anhydride peaks due to the carbonyl groups (peaks at 1859 and 1778 cm-1), and the appearance of carbonyl peaks at 1735 and 1704 cm-1 due to the formation of ester and acid respectively.

The product had very limited solubility in water.
The scheme below illustrates this synthesis:

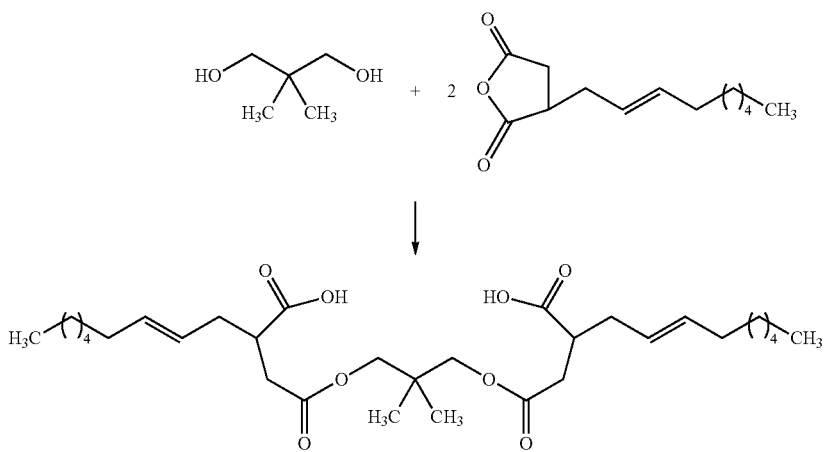

Example 3

Reaction Between Alkenylsuccinic Anhydride and Cyclohexylethanol

A reactor was charged with 2-cyclohexylethanol (5.716 g, 44.58 mmol) (Aldrich) and 2-(1-nonenyl) succinic anhydride (10 g, 44.58 mmol) (Aldrich). The mixture was stirred for about 1.75 hours at 130° C. under nitrogen. The product was then analyzed by IR. The sample was run in the "Attenuated Total Reflectance mode" placing the sample over a Germanium crystal. The IR spectra showed the almost complete disappearance of the initial anhydride peaks due to the carbonyl groups (peaks at 1863 and 1781 cm-1), and the appearance of carbonyl peaks at 1734 and 1703 cm-1 due to the formation of ester and acid respectively.

Other properties of the product were identified as follows:
Solubility in water at 25° C.>1%.
The scheme below illustrates this synthesis:

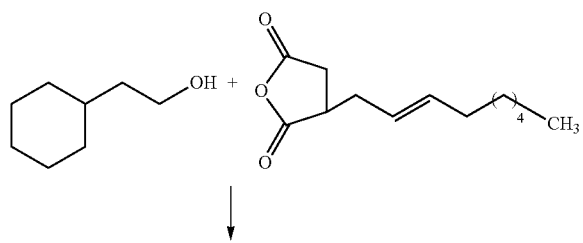

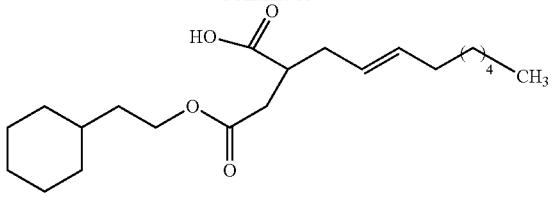

Example 4

Reaction Between Alkenylsuccinic Anhydride and Polyethylene Glycol

A reactor was charged with Poly(ethylene glycol), Mn=1000, (6.839 g, 6.839 mmol) (Aldrich) and Eka SA 210 brand alkylated succinic anhydride (4.822 g, 13.68 mmol). The Polyethylene glycol was dried beforehand in a vacuum oven at about 80° C. for 6 hours. The mixture was stirred for about 6 hours at 130° C. under nitrogen. The product was then analyzed by IR. The sample was run in the "Attenuated Total Reflectance mode" placing the sample over a Germanium crystal. The IR spectra showed the almost complete disappearance of the initial anhydride peaks due to the carbonyl groups (peaks at 1859 and 1782 cm-1), and the appearance of carbonyl peaks at 1731 cm-1 due to the formation of ester.

Other properties of the product were identified as follows:
Solubility in water at 25° C.>10%.
Cloud point (1% aqueous, pH>5)>90° C.
Cloud point (1% aqueous, pH<5) 10-40° C.
The scheme below illustrates this synthesis:

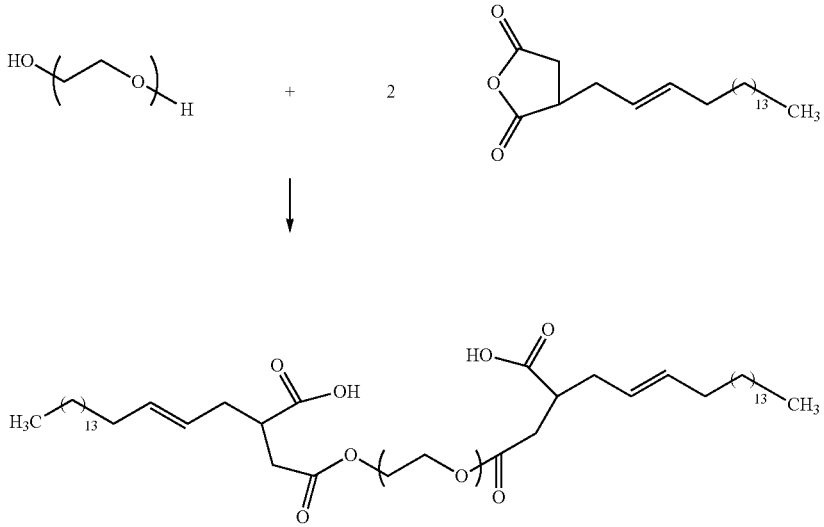

Example 5

Reaction Between Alkenylsuccinic Anhydride and Polyethylene Glycol

A reactor was charged with Poly(ethylene glycol) (Fluka) (molecular weigh 380-420) (12.82 g, 32 mmol) and Eka SA 210 brand alkylated succinic anhydride (22.58 g, 64 mmol).

The mixture was stirred for about 3 hours at 130° C. under nitrogen. The product was then analyzed by IR. The sample was run in the "Attenuated Total Reflectance mode" placing the sample over a Germanium crystal. The IR spectra showed the almost complete disappearance of the initial anhydride peaks due to the carbonyl groups (peaks at 1859 and 1778 cm-1), and the appearance of carbonyl peaks at 1735 cm-1 due to the formation of ester.

The primary constituent of the product mixture obtained has the structure shown below:

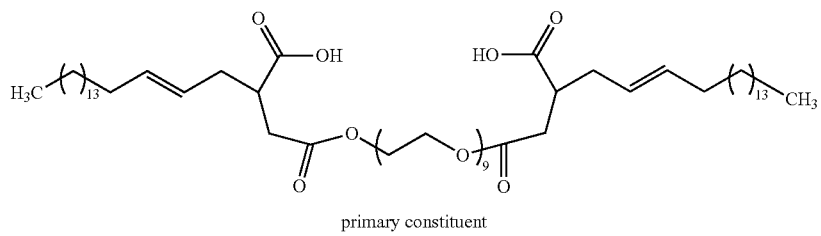

primary constituent

Other properties of the product were identified as follows:
Solubility in water at 25° C.>10%.
Cloud point (1% aqueous, pH>5)>90° C.
The scheme below illustrates this synthesis:

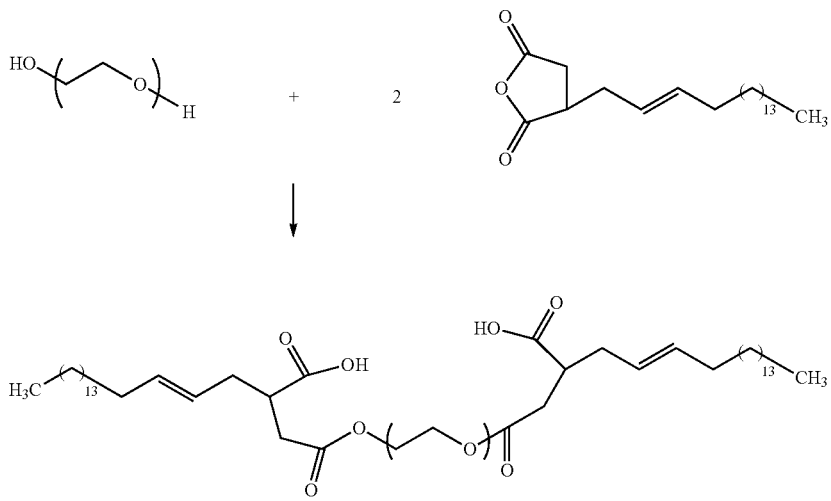

Example 6

Reaction Between an Ethylene Oxide/Propylene Oxide Block Copolymer and Alkenylsuccinic Anhydride A reactor was charged with PLURONIC® L64 (BASF) (8.8248 g, 3.04 mmol) and 2-(1-nonenyl) succinic anhydride (1.36 g, 6.09 mmol) (Aldrich). The mixture was stirred for about 6 hours at 130° C. under nitrogen. The product was then analyzed by IR. The sample was run in the "Attenuated Total Reflectance mode" placing the sample over a Germanium crystal. The IR spectra showed the almost complete disappearance of the initial anhydride peaks due to the carbonyl groups (peaks at 1859 and 1782 cm-1), and the appearance of carbonyl peaks at 1731 cm-1 due to the formation of ester.

Other properties of the product were identified as follows:
Solubility in water at 25° C.>10%.
Cloud point (1% aqueous, pH>5)>90° C.
The scheme below illustrates this synthesis:

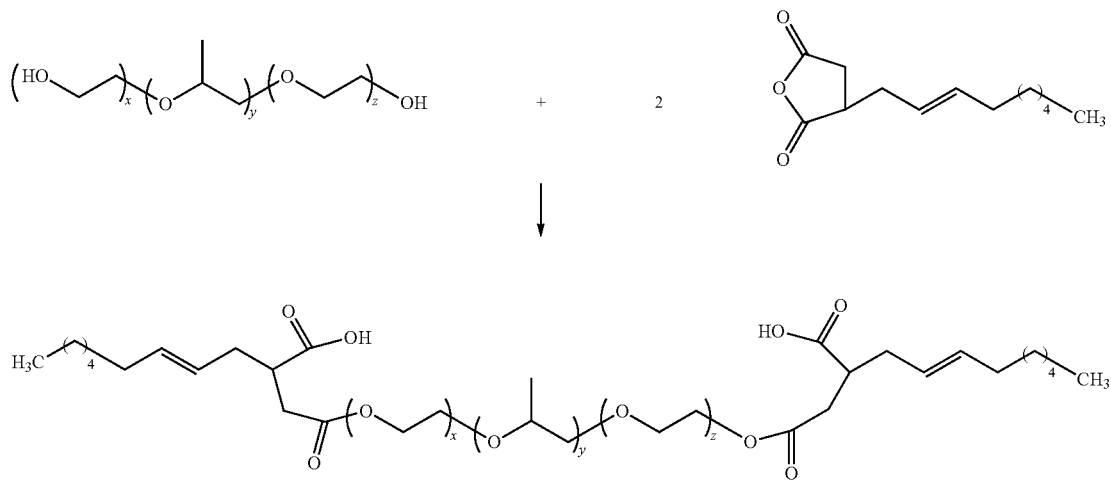

Example 7

Reaction Between Alkenylsuccinic Anhydride and Polyethylene Glycol Methyl Ether

A reactor was charged with Poly(ethylene glycol)methyl ether (Mn~550) Aldrich (10 g, 18.18 mmol) and 2-(1-nonenyl) succinic anhydride (4.843 g, 18.18 mmol), Aldrich. The mixture was stirred for about 3 hours at 130° C. under nitrogen. The product was then analyzed by IR. The sample was run in the "Attenuated Total Reflectance mode" placing the sample over a Germanium crystal. The IR spectra showed the almost complete disappearance of the initial anhydride peaks due to the carbonyl groups (peaks at 1855 and 1781 cm-1), and the appearance of carbonyl peaks at 1731 cm-1 due to the formation of ester.

Other properties of the product were identified as follows:
Solubility in water at 25° C.>10%.
Cloud point (1% aqueous, pH>5)>90° C.
Cloud point (1% aqueous, pH<5)<90° C.
The scheme below illustrates this synthesis:

Example 8

Reaction Between Polyetheramine and Alkenylsuccinic Anhydride

A reactor was charged with JEFFAMINE® ED-900 (XTJ-501) with MW=900 (HUNTSMAN) (10 g, 11.1 mmol), nonenyl succinic anhydride (5.919 g, 22.2 mmol) (Aldrich) and 15 ml of THF (Aldrich). The mixture was stirred for about 3 hour at room temperature. Then the solvent was stripped off under vacuum in a rotary evaporator. The product was analyzed by IR, which showed complete disappearance of the anhydride carbonyl peaks (1859 and 1778 cm-1) and the appearance of the amide and acid carbonyl bands (1645 and 1540 for amide I and II respectively, and 1731 cm-1 for acid).

Other properties of the product were identified as follows:
Solubility in water at 25° C.>10%.
Cloud point (1% aqueous, pH>5)>90° C.

The scheme below illustrates this synthesis:

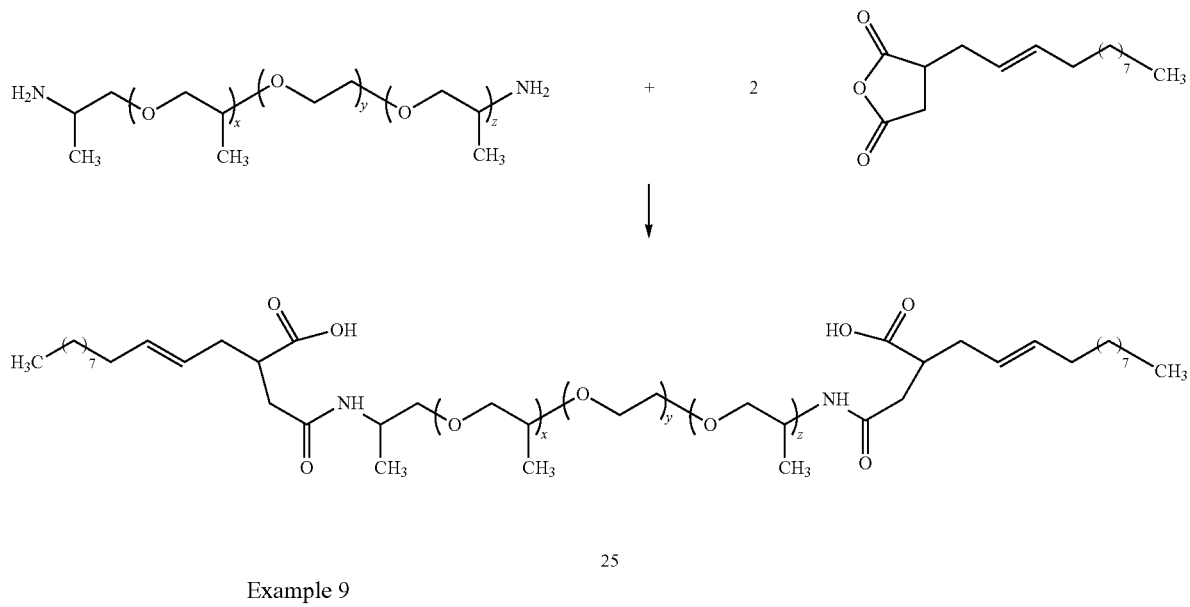

Example 9

Reaction Between an Aliphatic Diacid and a Polyetheramine

Under a nitrogen atmosphere, an oven-dried reactor was charged with anhydrous tetrahydrofurane (15 ml) (Aldrich), adipic acid (0.73 g, 5 mmol) Aldrich, JEFFAMINE® M-1000 (XTJ-506) with MW=1000 (HUNTSMAN) (10 g, 10 mmol) and dicyclohexylcarbodiimide (Aldrich) (2.269 g, 11 mmol). The mixture was stirred overnight at room temperature. A white precipitate was formed and was removed by vacuum filtration and discharged. The clear liquid residual that was obtained was stripped of from solvent under vacuum in the rotary evaporator and analyzed by IR. The IR spectra showed the almost complete disappearance of the initial acid band due to adipic acid (peak at 1692 cm-1), and the appearance of new peaks at 1653 and 1540 cm-1, corresponding to amide.

Other properties of the product were identified as follows:
Solubility in water at 25° C.>1%.
Cloud point (1% aqueous)>90° C.
The scheme below illustrates this synthesis:

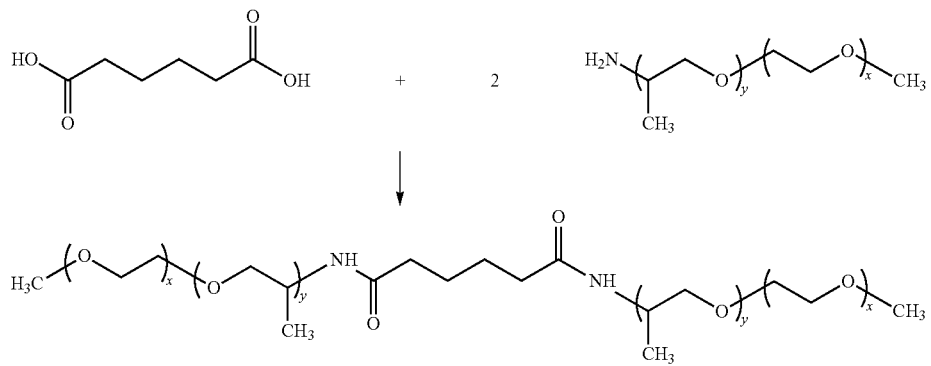

Example 10

Reaction Between Polyetheramine and Hydrophobic Glycidyl Ether

A reactor was charged with Glycidyl hexadecyl ether (Aldrich) (5.97 g, 20 mmol), JEFFAMINE® ED-2003 (XTJ-502) with MW=2000 (HUNTSMAN, Austin, Tex. 78752, USA) (9 g, 4.5 mmol) and 25 ml of isopropanol. The mixture was stirred for 5 hours under reflux and under nitrogen. Then the solvent was stripped off under vacuum. The reaction was monitored by IR following the disappearance of the 915 cm-1 peak (epoxy group) and the appearance of the broad peak at 3500 cm-1 (hydroxy group) The peak at 915 cm-1 disappeared almost completely with only very small traces left, indicating that the starting materials have reacted.

Other properties of the product were identified as follows:
Solubility in water at 25° C.~0.5%.

The scheme below illustrates this synthesis:

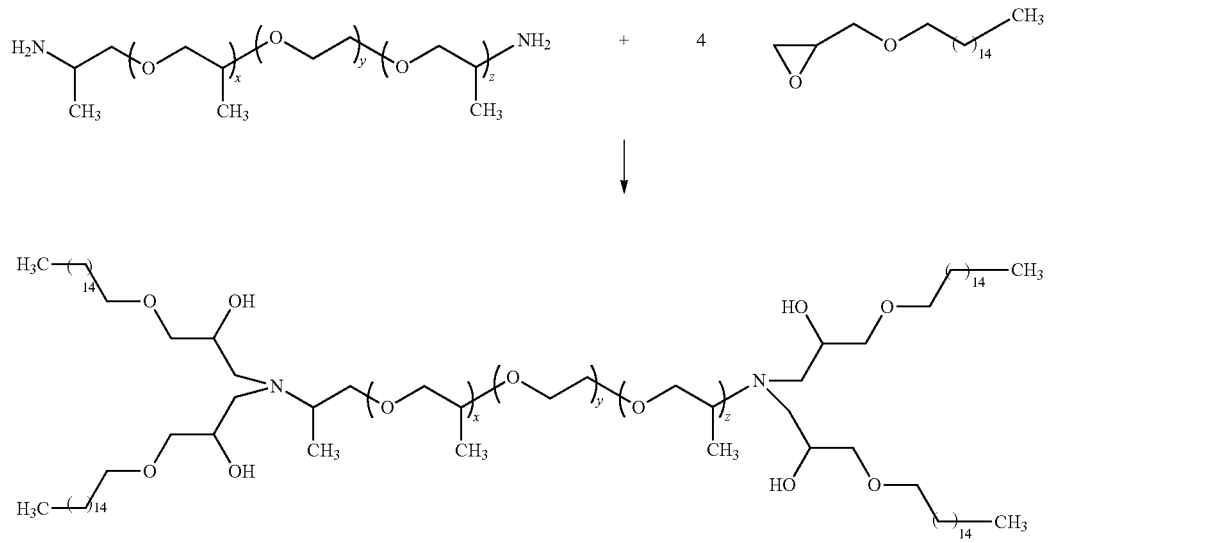

Example 11

Reaction Between Polyetheramine and Hydrophobic Glycidyl Ether

A reactor was charged with Glycidyl hexadecyl ether (Aldrich) (2.9851 g, 10 mmol), JEFFAMINE® M-1000 (XTJ-506) with MW=1000 (HUNTSMAN) (10 g, 10 mmol) and 25 ml of isopropanol. The mixture was stirred for 5 hours under reflux and under nitrogen. Then the solvent was stripped off under vacuum. The reaction was monitored by IR following the disappearance of the 915 cm-1 peak (epoxy group) and the appearance of the broad peak at 3500 cm-1 (hydroxy group) The peak at 915 cm-1 disappeared almost completely, with only very small traces left, indicating that the starting materials have reacted.

Other properties of the product were identified as follows:
Solubility in water at 25° C.>10%.
Cloud point (1% aqueous) 80-90° C.

The scheme below illustrates this synthesis:

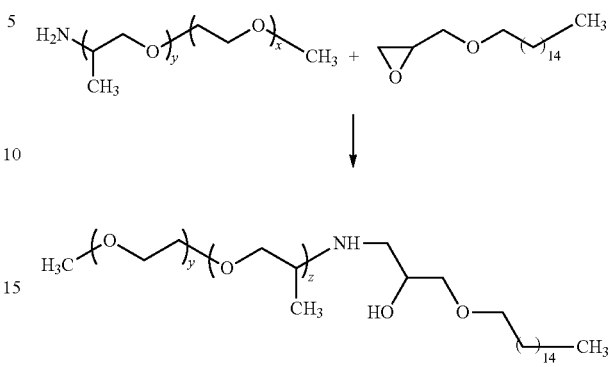

Example 12

Reaction Between Polyetheramine and Hydrophobic Glycidyl Ether

A reactor was charged with Glycidyl hexadecyl ether (Aldrich) (5.97 g, 20 mmol), JEFFAMINE® ED-600 (XTJ-500) with MW=600 (HUNTSMAN) (6 g, 10 mmol) and 24 ml of isopropanol. The mixture was stirred for 5 hours under reflux and under nitrogen. Then the solvent was stripped off under vacuum. The reaction was monitored by IR following the disappearance of the 915 cm-1 peak (epoxy group) and the appearance of the broad peak at 3500 cm-1 (hydroxy group) The peak at 915 cm-1 disappeared almost completely, with only very small traces left, indicating that the starting materials have reacted.

Other properties of the product were identified as follows:
Solubility in water at 25° C.>1%.
Cloud point (1% aqueous) 50-57° C.

The scheme below illustrates this synthesis:

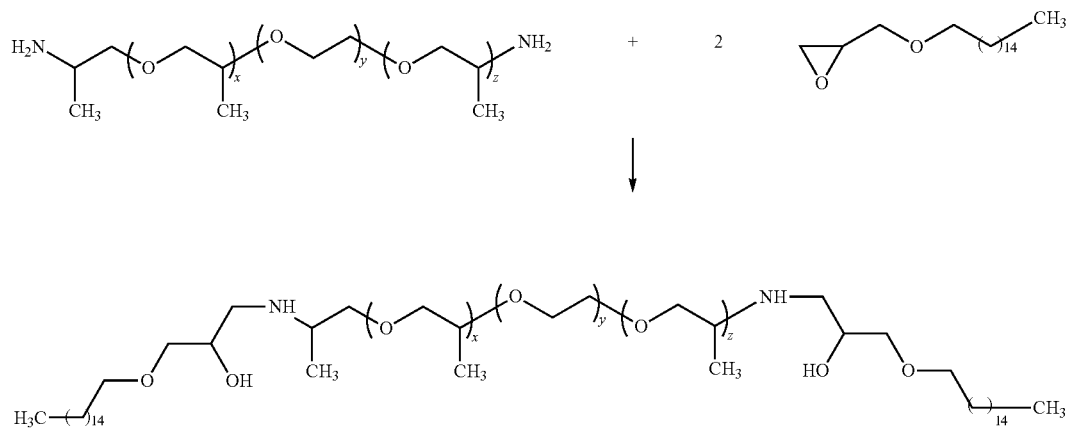

Example 13

Reaction Between Polyetheramine and Hydrophobic Glycidyl Ether

A reactor was charged with Glycidyl hexadecyl ether (Aldrich) (2.985 g, 10 mmol), JEFFAMINE® ED-2003 (XTJ-502) with MW=2000 (HUNTSMAN) (10 g, 5 mmol) and 26 ml of isopropanol. The mixture was stirred for 5 hours under reflux and under nitrogen. Then the solvent was stripped off under vacuum. The reaction was monitored by IR following the disappearance of the 915 cm-1 peak (epoxy group) and the appearance of the broad peak at 3500 cm-1 (hydroxy group) The peak at 915 cm-1 disappeared almost completely, with only very small traces left, indicating that the starting materials have reacted.

Other properties of the product were identified as follows:
Solubility in water at 25° C.>10%.
Cloud point (1% aqueous) 57-60° C.
The scheme below illustrates this synthesis:

Example 14

Surfactant Solutions Surface Activity

Surfactant molecules were tested for their ability to decrease the surface tension across the aqueous-organic interface. Interfacial tension (IFT) measurements were conducted using a KSV Sigma 702 tensiometer with a Du Nouys ring. Surfactant solutions were prepared at 1% by weight in accordance with Examples 4, 8, 13, 3 and 9, and adjusted to neutral pH with 5 M NaOH. Each aqueous surfactant solution was tested interfacing with air, toluene, Exxon ISOPAR M (blend of C13-C15 aliphatics) and light crude oil (API=37.4°). IFT values are reported in Table 1.

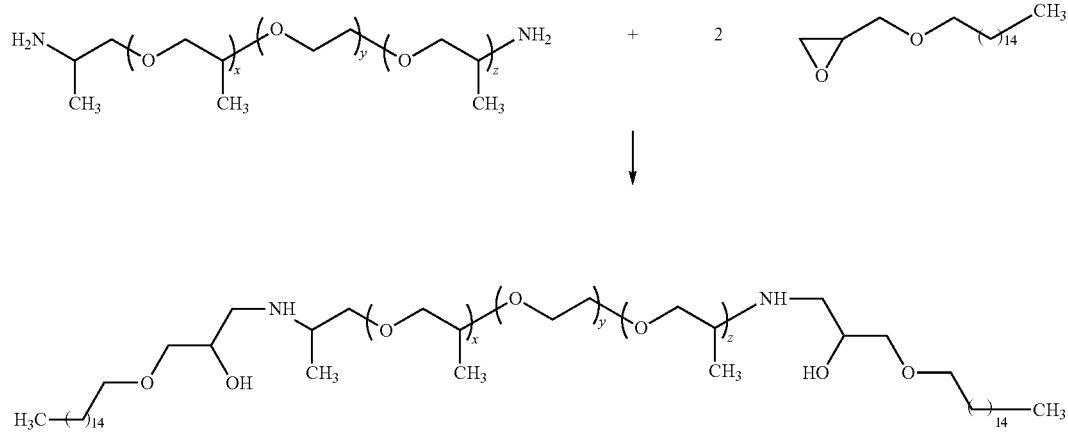

TABLE 1

Interfacial Tension Values for Aliphatic-based surfactants.

| Surfactant Name | IFT w/ air [mN/m] | IFT w/ Toluene [mN/m] | IFT w/ ISOPAR [mN/m] | IFT w/ Crude Oil [mN/m] |
|---|---|---|---|---|
| Deionized Water | 71.88 | 33.12 | 72.38 | a |
| Poly(ethylene glycol)-bis-[3-(2-nonen-1-yl)succinic acid] ester | 39.10 | 8.13 | 6.18 | 3.69 |
| Polyetherdiamine-bis-[3-(2-dedecen-1-yl succinic acid] amide | 43.20 | 1.50 | 10.60 | 7.37 |
| N,N'-bis(3-hexadecyl ether-2-hydroxypropyl)polyetherdiamine | 38.40 | 6.67 | 15.95 | 7.61 |
| 2-(nonen-1-yl)succinic acid mono (2-cyclohexylethyl) ester | 28.68 | <0.01 b | 0.09 | <0.01 |
| N(1),N(6)-dipolyether hexane diamide | 40.05 | 12.90 | 7.58 | 7.89 | a Interfacial tension exceeded maximum device limit of XXX mN/m.
b Interfacial tension below minimum device limit of 0.01 mN/m.

As observed in Table 1, the 1% solution of the molecule prepared in accordance with Example 3 is of particular interest because of its low IFT values with all three organic liquids. For certain applications, such as EOR, it is desirable to have such low interfacial tensions with crude oils because EOR surfactant solutions are often used to recover crude oil that is trapped within the capillaries of rock formations.

Example 15

Surfactant Stability

Application of the synthesized surfactants are tested for their ability to emulsify different density oil samples while also yielding a stable mixture that does not phase separate. In the experiments listed below, a 2 mL sample of heavy oil (API=15.0°) was combined with 2 mL samples of 1% by weight surfactant solutions, including a test surfactant solution, and two commercial surfactants. The test surfactant solution was prepared by dissolving 1.01 grams of the molecule prepared in accordance with Example 3 in 100 mL of deionized water, and neutralizing it with 0.547 grams of 5M NaOH. The mixture was then shaken by hand for 10 minutes and set aside. The commercial surfactants Igepal DM-970 and Tergitol 15-S-30 were used to form 1% by weight surfactant solutions to compare with the test surfactant. Deionized water was used as the control. Photographs and phase height measurements were taken at 5, 30, and 60 minutes as well as 24 hours after mixing. Table 2 displays the percentage of the solution occupied by emulsion phase over time for each surfactant (test surfactant and two commercial surfactants). FIG. 1 shows the behavior of the emulsion over time, and shows a control sample containing DI-water (without surfactant). This example demonstrates that the synthesized surfactant of the present invention are capable of stabilizing heavy oil over long periods of time.

TABLE 2

Phase stability of surfactant solutions compared to commercial products.

| Surfactant solution | % mixture volume occupied by emulsion | | | |
|---|---|---|---|---|
| | 5 min | 30 min | 60 min | 1 day |
| Test surfactant (Example 3) | 93 | 79 | 64 | 36 |
| Igepal DM-970 | 21 | 14 | 14 | 14 |
| Tergitol 15-S-30 | 21 | 14 | 14 | 7 |
| Deionized water control | 21 | 14 | 14 | 7 |

Example 16

Surfactant Switchability by pH Variation

Surfactant switchability can be induced by the adjustment of mixture pH. Surfactant solutions that exhibit emulsifying characteristics at neutral pH can be deactivated from surface activity when the pH becomes acidic. This will allow for controlled recovery of oil from an otherwise stable emulsion. A test surfactant was compared to the commercial surfactant Tergitol 15-S-7. The surfactant solution was prepared by dissolving the molecule prepared in accordance with Example 3 in deionized water and adjusting the pH to neutral by the addition of 5 M NaOH. Two oil mixtures were prepared for each surfactant solution: initially the two mixtures had neutral pH, but after the vials were agitated and emulsion was formed, a few drops of HCl 10M was added to one of the vials to decrease the pH to ~3.

In each case, 2 mL of heavy oil (API=15.0°) was added to 2 mL of 1% by weight surfactant solution, and the vial was agitated to mix the components. Photographs of the vials were taken after 5, 30, 60 minutes and 24 hours after mixing, along with measurements of the height of vial occupied by water phase and emulsion phase. Table 3 displays the percentage of the solution occupied by the emulsion phase over time for the test surfactant solution, the commercial surfactant (Tergitol 15-S-7), and a control sample containing deionized-water and oil (without surfactant). The example shows that the surfactants of this invention can emulsify-demulsify oil depending on the pH of the mixture.

TABLE 3

Comparison of emulsion stability at neutral and acidic pH.

| Surfactant solution | Acid | pH | % mixture volume occupied by emulsion | | | |
|---|---|---|---|---|---|---|
| | | | 5 min | 30 min | 60 min | 1 day |
| Test (Example 3) | No | 9 | 100 | 99 | 93 | 43 |
| Test (Example 3) | yes | 1 | 0 | 0 | 0 | 0 |
| Tergitol 15-S-7 | No | 6 | 96 | 93 | 86 | 36 |
| Tergitol 15-S-7 | Yes | 1 | 93 | 64 | 50 | 29 |
| DI-Water | No | 6 | 0 | 0 | 0 | 0 |
| DI-Water | Yes | 1 | 0 | 0 | 0 | 0 |

Figure 2:
FIG. 2 shows comparison photographs of solutions prepared at neutral and acidic pH.

FIG. 2 shows the behavior of the emulsion with and without acid after 5 minutes along with a control sample containing DI-water (without surfactant) and a 1% solution of a commercial surfactant Tergitol 15-S-7.

In addition, a 105 mL sample of heavy oil (API=15.0°) was combined with 45 mL of a 1% by weight solution of the test surfactant (prepared in accordance with Example 3), producing a 70:30 oil to water mixture. The mixture was gently stirred until it was observed it achieved a single liquid phase. Previously, the viscosity of the neat heavy oil sample was measured at 3431 cP using a Brookfield DVIII+ Rheometer. The 70:30 mixture exhibited a viscosity of 100.2 cP. Next, 1 mL of 10 M HCl was added and the mixture was stirred gently, while observing phase separation of the oil and water. The oil sample was decanted from the container and obtained the same viscosity measurement as the untreated heavy oil sample.

Example 17

Removal of Crude Oil from Sand Surfaces

Samples of oil-contaminated sand were prepared by mixing 50/70 mesh sand with a sample of light crude oil (API=28.6°). 100 grams of sand were mixed with 10 grams of oil using a stir rod, until the solid sand was thoroughly coated and the sample appeared uniform. A muffle furnace set at 650° C. was used to heat a 5 gram sample of oil-contaminated sand for 3 hours to determine the total organic content. Additionally, 1% by weight solutions of molecules prepared in accordance with Example 13 and Example 3 were prepared at neutral pH by the addition of small amounts of 5 M NaOH. Samples were stirred using magnetic stir bars until each surfactant was completely dissolved in solution. In a separate 200 mL jar, 150 mL of each surfactant solution was added to 30 grams of oil-contaminated sand.

After addition of the 1% solution from Example 13, it was observed that, after moderate agitation by shaking, the contaminant crude oil was significantly removed from the sand surface. Upon initially shaking the jar, the oil separated from the sand surface and became emulsified in the aqueous solution. After leaving the jar stationary for approximately 5 minutes, the oil remained emulsified in the aqueous phase, leaving a clean, settled layer of sand at the bottom. After approximately 30 minutes, slight phase separation began to occur with oil forming on the top layer of the water phase.

Similarly, 30 grams of oil-contaminated sand (10% by weight) was washed with 150 mL of a 1% surfactant solution from Example 3. Upon initially adding the aqueous solution to the jar, it was immediately observed that oil droplets began to separate from the sand on the bottom of the jar and rise to the water-air interface. Even with only slight agitation of the jar by tipping, nearly all of the contamination on the sand was removed. Total oil removal percentages are presented in Table 4.

TABLE 4

Oil Removal from Oily Sand

| Solution used to wash Oily-sand | % Oil remaining in Oily-sand After Wash | % Oil Recovery by Washing |
| --- | --- | --- |
| None | 9.17% | |
| DI Water | 7.90% | 13.86% |
| 1% Example 13 | 0.75% | 91.81% |
| 1% Example 3 | 0.53% | 94.19% |

Example 18

Reaction Between an Ethylene Oxide/Propylene Oxide Block Copolymer and Phenyl Succinic Anhydride A reactor was charged with phenyl succinic anhydride (0.564 g, 10.52 mmol) and Pluronic L35 (10 g, 5.26 mmol). The mixture was stirred for about 4 hours at 130° C. under nitrogen. The product was then analyzed by IR which showed almost complete disappearance of the anhydride carbonyl peaks (1859 and 1785 cm-1) and the appearance of the ester and acid carbonyl band (1731 cm-1).

Other properties of the product were identified as follows:

Solubility in water at 25° C.>10%.

Cloud point (1% aqueous, pH~8)>100° C.

Cloud point (1% aqueous, pH~2) 60-100° C.

The scheme below illustrates this synthesis:

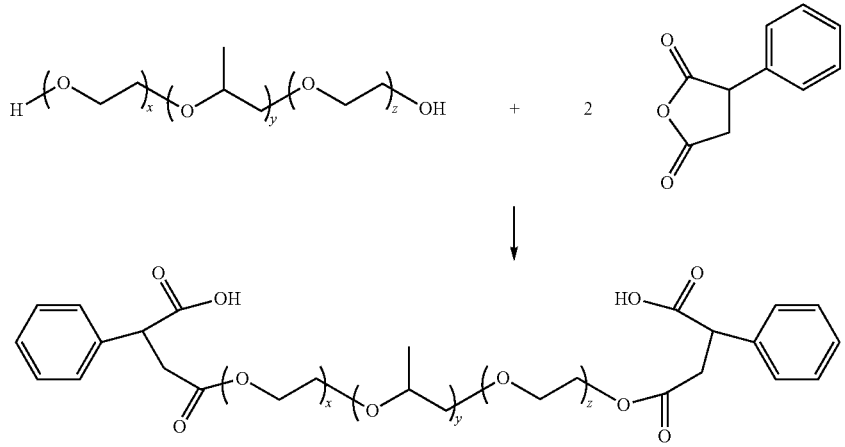

Example 19

Reaction Between an Ethylene Oxide/Propylene Oxide Block Copolymer and Phenyl Succinic Anhydride A reactor was charged with phenyl succinic anhydride (0.9746 g, 18.2 mmol) and Pluronic L31 (10 g, 9.1 mmol). The mixture was stirred for about 2.5 hours at 130° C. under nitrogen. The product was analyzed by IR which showed almost complete disappearance of the anhydride carbonyl peaks (1859 and 1785 cm-1) and the appearance of the ester and acid carbonyl band (1731 cm-1).

Other properties of the product were identified as follows:
Solubility in water at 25° C.>10%.
Cloud point (1% aqueous, pH~8)<64° C.

The scheme below illustrates this synthesis:

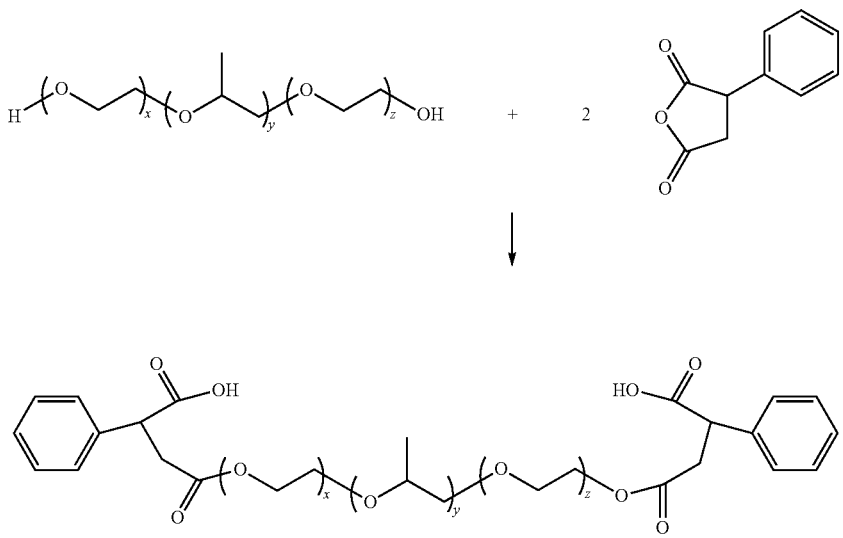

Example 20

Reaction Between an Aromatic Diacid and a Polyetheramine

Under a nitrogen atmosphere, an oven-dried reactor was charged with anhydrous dichloromethane (25 ml), terephthalic acid (0.831 g, 5 mmol), Jeffamine M-1000 brad polyethermonoamine (10 g, 10 mmol) and dicyclohexylcarbodiimide (2.269 g, 11 mmol). The mixture was stirred overnight at room temperature. A white precipitate was formed. This material through a Buchner funnel. The clear liquid residual that was obtained was stripped of from solvent under vacuum. The liquid residual product was analyzed by IR, which showed that a fraction of the starting terephthalic acid peak was present at 1700 cm-1, and that new amide peaks appeared at 1653 and 1536 cm-1, consistent with the reaction between the aromatic diacid and the polyetheramine proceeded partially. The scheme below illustrates this synthesis:

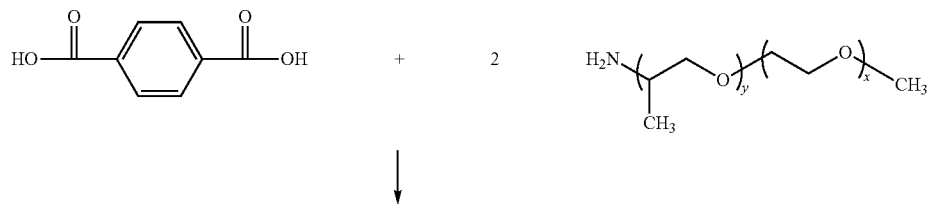

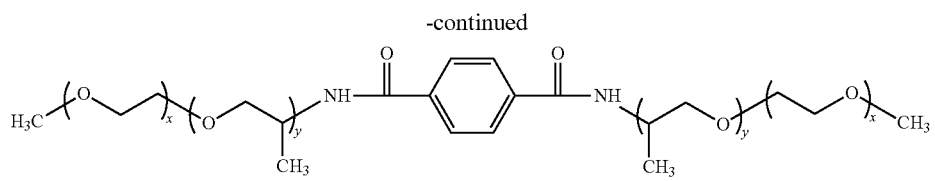

Example 21

Preparation of Secondary Amine by Reacting a Polyetheramine and Phenyl Glycidyl Ether A reactor was charged with phenyl glycidyl ether (3 g, 20 mmol), Jeffamine M-1000 brand polyethermonoamine (10 g, 10 mmol) and 25 ml of isopropanol. The mixture was stirred for 5 hours under reflux and under nitrogen. Then the solvent was stripped off under vacuum.

The reaction was monitored by IR following the disappearance of the 915 cm-1 peak (epoxy group) and the appearance of the broad peak at 3500 cm-1 (hydroxy group).

Other Properties:
Solubility in water at 25° C.>10%.
Cloud point (1% aqueous) 57-60° C.
The scheme below illustrates this synthesis:

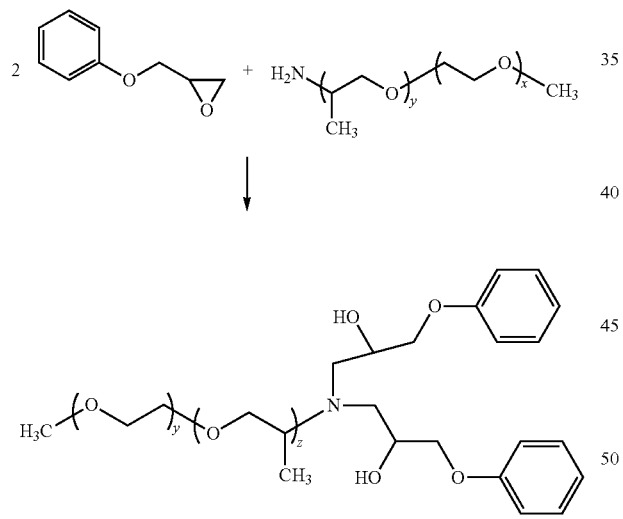

Example 22

Interfacial Tension (IFT) Measurements of Surfactants

Solutions of surfactants, listed in Table 5 below, were dissolved in aqueous solution at 1% by weight. Deionized water was used as the control. Each surfactant was formulated as described above. The pH of each solution was adjusted to 9 by the addition of 1 M sodium hydroxide. Using a KSV Sigma 702 tensiometer, the interfacial tension was measured for each solution at the interface with air, toluene and Exxon ISOPAR M fluid. Values are reported in Table 5.

TABLE 5

Table 5: Interfacial tension measurements for 1% surfactant solutions at the interface of air, toluene and ISOPAR

| | Compound | Example | IFT w/ air [mN/m] | IFT w/ Toluene [mN/m] | IFT w/ ISOPAR [mN/m] |
|---|---|---|---|---|---|
| 1 | Deionized Water | Control | 71.88 | 33.12 | 72.38 |
| 3 | 1-[methoxypoly(oxyethylene/oxypropylene)-2-propylamino]-3-phenoxy-2-propanol | 21 | 41.50 | 0.93 | 5.84 |
| 4 | N,N-bis(3-phenoxy-2-hydroxypropyl)polyetheramine | 18 | 45.77 | 0.18 | 7.41 |

Example 23

Surfactant Properties

A solution prepared in accordance with Example 21 was dissolved into aqueous solution at 1% by weight and the pH was adjusted to 9 by the addition of 1 M sodium hydroxide, to form a surfactant solution. 2 mL of light crude (API gravity index=28) was emulsified at 50:50 volume ratio with the surfactant solution. The mixture was amply shaken and then left to sit for one hour. After an hour, no phase separation had occurred. After 2 days of leaving the emulsion to rest, about 1 mL of water had been separated and about 0.5 mL of oil had been separated. An emulsion layer remained in between the separated water and oil layers.

Example 24

Oily Sand Treatment 30 grams of washed sand (50/70 mesh) was mixed with 3 grams of light crude oil (API gravity index=28) by stirring until the oil was evenly distributed over the surface of the sand. For this experiment, the surfactant prepared in accordance with Example 21 (Surfactant B) was tested. 150 mL of a 1% surfactant solution was mixed with the oily sand by sealing in a jar and shaking by hand at a moderate pace for 5 minutes. The contents of the jar were left to sit for 1 hour and then the liquid layer was decanted from the sand. The jar was placed in an oven under vacuum at 100° C. for 3 hours, then cooled to room temperature. A sample of the dried sand was weighed and placed in a muffle furnace at 650° C. for 3 hours, then reweighed to determine the total remaining weight of hydrocarbon on the sand surface. Table 6 summarizes the effect of the surfactant solutions.

TABLE 6

| Solution used to wash Oily-sand | % Oil remaining in Oily-sand After Wash | % Oil Recovery by Solution |
| --- | --- | --- |
| None | 8.83% | |
| Deionized water | 7.90% | 10.54% |
| 1% Surfactant B | 1.60% | 81.93% |

Example 25

Surfactant Compound in Sodium Hydroxide Solution 75.57 g of tap water and 3.10 g of 50% Sodium hydroxide were added to a beaker. The solution was mixed until homogeneous. 21.33 g product obtained in Example 5 was slowly added while stirring the solution. The mixing was continued until a homogeneous solution is obtained. The primary constituent in the solution has the structure shown below:

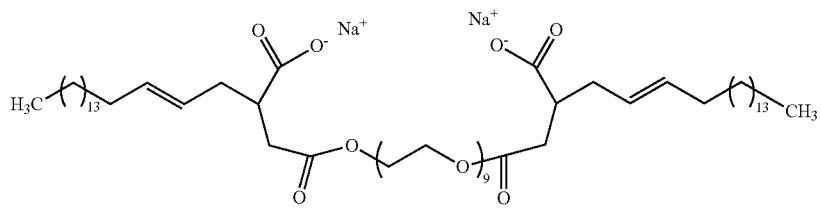

Primary constituent
22 weight percent in aqueous solution

EQUIVALENTS

While specific embodiments of the subject invention have been discussed, the above specification is illustrative and not restrictive. Many variations of the invention will become apparent to those skilled in the art upon review of this specification. Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth herein are approximations that can vary depending upon the desired properties sought to be obtained by the present invention.

While this invention has been particularly shown and described with references to preferred embodiments thereof, it will be understood by those skilled in the art that various changes in form and details may be made therein without departing from the scope of the invention encompassed by the appended claims.

What is claimed:

1. A method for extracting oil from an oil mixture comprising:
   (a) adding a compound to an oil mixture, wherein the compound has the Formula IIb:

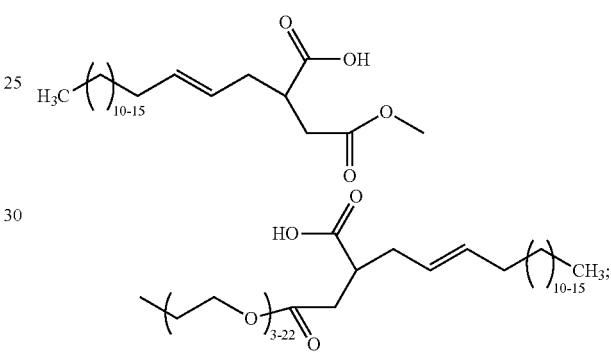

and (b) collecting the oil.

2. The method of claim 1, wherein the compound is:

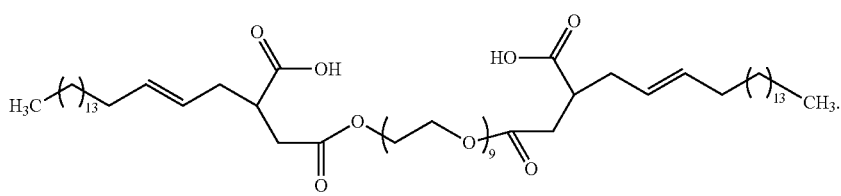

3. The method of claim 1, wherein the compound is in an aqueous solution having a pH greater than 8.

4. The method of claim 1, wherein the solution comprises sodium hydroxide.

* * * * *

UNITED STATES PATENT AND TRADEMARK OFFICE
CERTIFICATE OF CORRECTION

PATENT NO. : 9,315,718 B2  
APPLICATION NO. : 14/608606  
DATED : April 19, 2016  
INVENTOR(S) : David S. Soane et al.

Page 1 of 1

It is certified that error appears in the above-identified patent and that said Letters Patent is hereby corrected as shown below:

In the Claims

Column 40, Claim 1: delete " 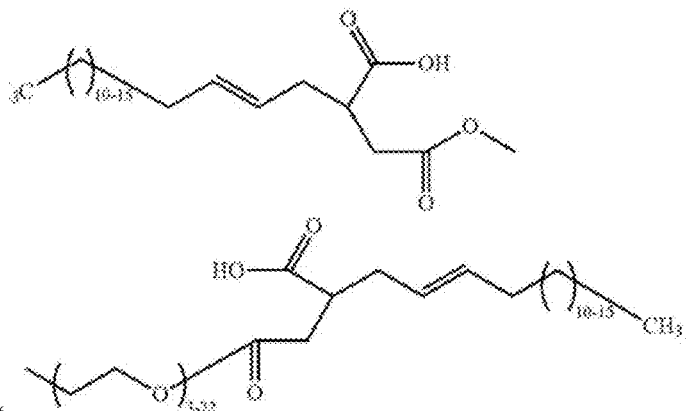 " and replace with -- 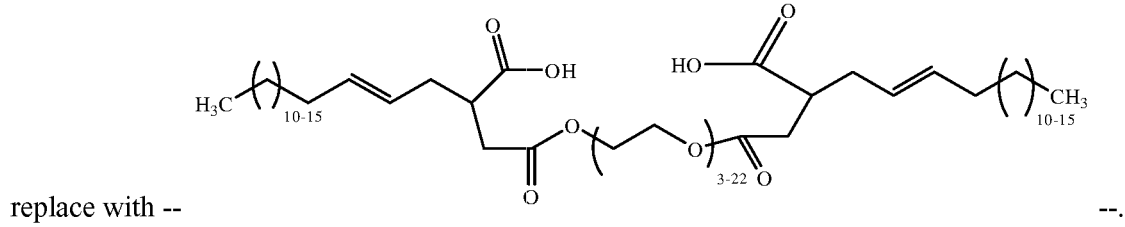 --.

Signed and Sealed this  
Fifth Day of July, 2016

Michelle K. Lee  
*Director of the United States Patent and Trademark Office*